United States Patent
Wessol et al.

(10) Patent No.: US 6,965,847 B2
(45) Date of Patent: *Nov. 15, 2005

(54) METHODS AND COMPUTER READABLE MEDIUM FOR IMPROVED RADIOTHERAPY DOSIMETRY PLANNING

(75) Inventors: Daniel E. Wessol, Bozeman, MT (US); Michael W. Frandsen, Helena, MT (US); Floyd J. Wheeler, Rigby, ID (US); David W. Nigg, Idaho Falls, ID (US)

(73) Assignee: Battelle Energy Alliance, LLC, Idaho Falls, ID (US)

(*) Notice: Subject to any disclaimer, the term of this patent is extended or adjusted under 35 U.S.C. 154(b) by 839 days.

This patent is subject to a terminal disclaimer.

(21) Appl. No.: 09/814,299

(22) Filed: Mar. 21, 2001

(65) Prior Publication Data

US 2002/0046010 A1 Apr. 18, 2002

Related U.S. Application Data

(63) Continuation-in-part of application No. 09/063,736, filed on Apr. 21, 1998.
(60) Provisional application No. 60/191,079, filed on Mar. 21, 2000.

(51) Int. Cl.$^7$ ............................................. G06F 9/455
(52) U.S. Cl. ........................... 703/5; 345/424; 382/133
(58) Field of Search .................... 703/5, 6, 7; 382/133, 382/132; 345/424; 600/477, 439; 395/124; 424/1.25; 378/41; 250/370, 474, 370.09, 474.1; 73/633

(56) References Cited

U.S. PATENT DOCUMENTS

| | | | |
|---|---|---|---|
| 3,987,281 A | | 10/1976 | Hodes |
| 4,398,251 A | | 8/1983 | LeMay |
| 4,675,150 A | | 6/1987 | Russell, Jr. et al. |
| 5,101,475 A | * | 3/1992 | Kaufman et al. ............ 395/124 |
| 5,341,292 A | | 8/1994 | Zamenhof |
| 5,392,319 A | | 2/1995 | Eggers |
| 5,442,733 A | * | 8/1995 | Kaufman et al. ............ 345/424 |

(Continued)

OTHER PUBLICATIONS

Nigg, David W., Methods for Radiation Fose Distribution Analysis and Treatment Planning in Boron Neutron Capture Thereapy, Int J. Radiation Oncology Bio. Phys. vol. 28., No. 5, pp. 1121–1134, 1994.

(Continued)

*Primary Examiner*—Kevin J. Teska
*Assistant Examiner*—Kandasamy Thangavelu
(74) *Attorney, Agent, or Firm*—Trask Britt, P.C.

(57) ABSTRACT

Methods and computer readable media are disclosed for ultimately developing a dosimetry plan for a treatment volume irradiated during radiation therapy with a radiation source concentrated internally within a patient or incident from an external beam. The dosimetry plan is available in near "real-time" because of the novel geometric model construction of the treatment volume which in turn allows for rapid calculations to be performed for simulated movements of particles along particle tracks therethrough. The particles are exemplary representations of alpha, beta or gamma emissions emanating from an internal radiation source during various radiotherapies, such as brachytherapy or targeted radionuclide therapy, or they are exemplary representations of high-energy photons, electrons, protons or other ionizing particles incident on the treatment volume from an external source. In a preferred embodiment, a medical image of a treatment volume irradiated during radiotherapy having a plurality of pixels of information is obtained.

42 Claims, 9 Drawing Sheets

U.S. PATENT DOCUMENTS

| | | | |
|---|---|---|---|
| 5,458,125 A | | 10/1995 | Schweikard |
| 5,493,595 A | * | 2/1996 | Schoolman .................. 378/41 |
| 5,498,876 A | * | 3/1996 | Moscovitch ............. 250/474.1 |
| 5,548,694 A | | 8/1996 | Gibson |
| 5,630,786 A | | 5/1997 | Griffin et al. |
| 5,647,663 A | | 7/1997 | Holmes |
| 5,678,556 A | * | 10/1997 | Maki et al. ................. 600/477 |
| 5,703,918 A | | 12/1997 | Hiismaki et al. |
| 5,821,541 A | * | 10/1998 | Tumer .................. 250/370.09 |
| 5,870,697 A | | 2/1999 | Chandler et al. |
| 5,976,066 A | | 11/1999 | Yanch et al. |
| 6,008,813 A | * | 12/1999 | Lauer et al. ................. 345/424 |
| 6,029,079 A | | 2/2000 | Cox et al. |
| 6,078,681 A | * | 6/2000 | Silver ......................... 382/133 |
| 6,083,167 A | * | 7/2000 | Fox et al. ................... 600/439 |
| 6,216,540 B1 | * | 4/2001 | Nelson et al. ................ 73/633 |
| 6,345,114 B1 | * | 2/2002 | Mackie et al. ............. 382/132 |
| 6,589,502 B1 | * | 7/2003 | Coniglione ................ 424/1.25 |

OTHER PUBLICATIONS

Nori et al., Current Issues in Techniques of Prostate Brachytherapy, 13(6) Seminars in Surgical Oncology, pp 444–446, 1997.

International Search Report dated Sep. 27, 2002, 4 pages.

* cited by examiner

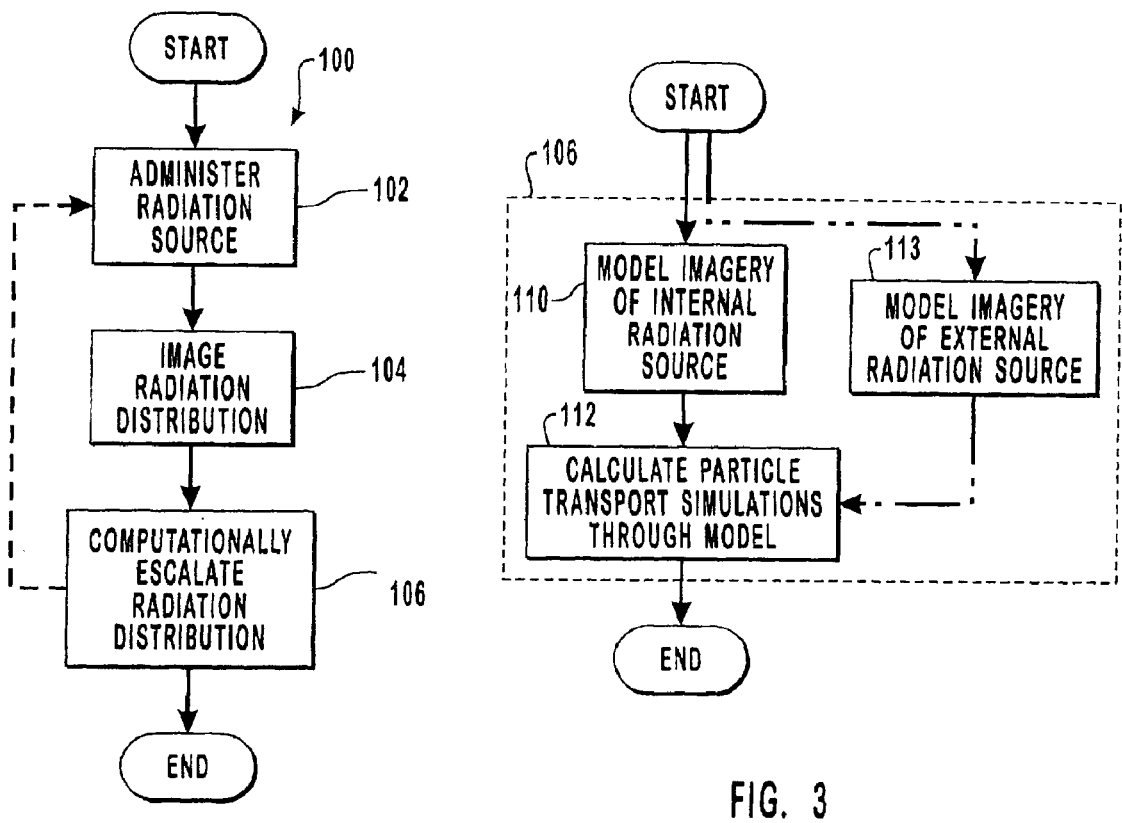
FIG. 2
FIG. 3
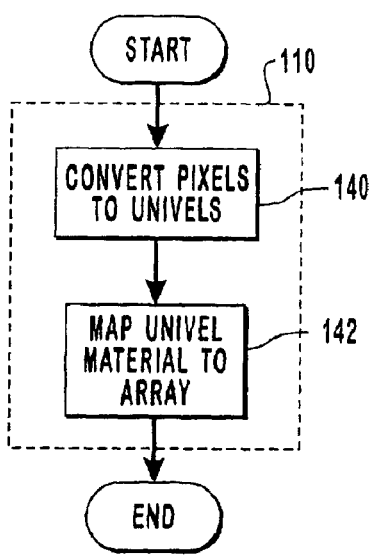
FIG. 4

METHODS AND COMPUTER READABLE MEDIUM FOR IMPROVED RADIOTHERAPY DOSIMETRY PLANNING

RELATED APPLICATIONS

This application claims priority from U.S. provisional application Ser. No. 60/191,079 filed Mar. 21, 2000 and is a continuation-in-part of U.S. application Ser. No. 09/063,736, filed Apr. 21, 1998, which are incorporated herein by reference.

CONTRACTUAL ORIGIN OF THE INVENTION

The United States Government has certain rights in this invention pursuant to Contract No. DE-AC07-94ID13223, DE-AC07-99ID13727, and Contract No. DE-AC07-05ID14517 between the United States Department of Energy and Battelle Energy Alliance, LLC.

BACKGROUND OF THE INVENTION

Field of the Invention

The present invention relates generally to radiation therapy and specifically to the dosimetric planning thereof. More specifically, the present invention relates to the macrodosimetry planning for specific radiotherapies, such as targeted radionuclides and brachytherapy, having radiation sources concentrated internally within a patient, as well as to external-beam photon radiotherapy. Even more specifically, the present invention relates to methods and computer readable medium for computationally enlarging the dose distributions of a treatment volume irradiated during various therapies.

Copyrighted Materials

A portion of the disclosure of this patent document contains materials to which a claim of copyright protection is made. The copyright owner has no objection to the reproduction by anyone of the patent document or the patent disclosure as it appears in the Patent and Trademark Office patent file or records, but reserves all other rights with respect to the copyrighted work.

Relevant Technology

Many forms of radiation therapy are known in the treatment of afflictions where the benefits of destroying diseased tissue outweigh the risk of damage to healthy tissue. Some of the more common therapies in the treatment of various cancers, for example, include X-rays, neutron capture therapy (NCT), targeted radionuclides and brachytherapy. Since healthy tissue of both the physician and patient is potentially subject to damage during the administration of the radiation, it is usually a prerequisite of radiotherapy to substantially predict the planned radiation dosage before the actual administration thereof.

Although many methods are available for planning the radiation dosage, a fundamental difference with regard to the source of the radiation exists for the therapies. In some therapies, such as X-rays, the radiation source is external to the patient. In others, such as brachytherapy and targeted radionuclides, the radiation source is concentrated internally within the patient. In still others, such as NCT, it is a hybrid. The neutrons are received from an external source, whereas the neutron capture agent is internal within the patient. All of which affect the radiation planning thereof.

Regardless of the radiation source, when predicting radiation dosage, radiation transport modules, typically in the form of computer programs, are used to simulate radiation distribution through a geometric representation of the radiation or treatment volume. In this manner, physicians are equipped with instruments to create and analyze endless hypothetical scenarios. Ultimately, this improves patient treatment.

The basic idea is to solve the fixed-source form of a transport equation by randomly selecting particles from a specified source that may be either internal or external to the body (i.e., the radiation source) and tracking each selected particle through the geometric representation until it is either captured by a material of the geometric representation, scattered or is exited therefrom. Typically, the particle is tracked along a particle track or path. Pseudo random numbers are often used to determine whether the particle is captured, exited or scattered.

In general, if capture or exiting occurs, the particle tracking is terminated. If scattering occurs, a new particle tracking begins from the position where the scatter occurred until that particle is either captured, exited or scattered. Eventually all particles are either captured or exited from the model.

Conventionally, however, the generation of geometric models has been limited because some methods do not base their information upon actual medical imagery. Some other methods only model a few anatomical materials of a patient. With either method, inaccuracy in modeling occurs because all known information of a patient is not utilized and correspondence to an actual patient is lacking. Ultimately, this limits the dosimetry planning for actual patients.

Conventional computational methods for tracking particles through the geometric model also exhibit shortcomings. For example, the fastest computations report analysis times as numerous hours in length for some complex applications. Since time is critical in the dosimetry planning for in vivo applications during clinical use, hours are unacceptably long.

As for brachytherapy in the treatment of prostate cancer, for example, several groups have documented the inadequacies of using a nomogram and their associated mathematical formulas for predicting radiation for the entire prostate gland with sources such as Iodine-125 and Palladium-103. See, e.g., Nori, D., and Moni, J., *Current Issues in Techniques of Prostate Brachytherapy,* 13(6) Seminars in Surgical Oncology, 444, 446 (1997).

Accordingly, it is desirable to improve the computational methods used in planning radiation dosages.

OBJECTS AND SUMMARY OF THE INVENTION

It is, therefore, an object of the present invention to provide improved methods for analytically computing dosimetry plans for use in radiotherapy planning.

It is another object of the present invention to improve methods for geometrically modeling a treatment volume irradiated during various therapies and for calculating simulated particle transport through the model.

It is still another object of the present invention to improve methods for geometrically modeling a treatment volume irradiated during various therapies by using all available anatomical information for various structures in the volume.

It is yet another object of the present invention to decrease the computational times required for calculating simulated particle transport through a geometrically modeled irradiated volume, especially during clinical use for in vivo applications.

It is still yet another object of the present invention to provide improved methods for geometrically modeling a treatment volume irradiated during various therapies and for calculating simulated particle transport through the model for radiation sources concentrated internally within a patient, hence concentrated within the model.

It is a further object of the present invention to provide improved geometric models for treatment volumes irradiated during various therapies that more closely approximate pertinent medical imagery.

It is an even further object of the present invention to provide improved methods of geometrically modeling treatment volumes irradiated during various therapies by using any available pertinent medical imagery.

It is still a further object of the present invention to provide improved methods for geometrically modeling a treatment volume irradiated during various therapies that does not substantially inhibit calculational times for simulated particle transport through the model as additional geometric elements used in the model are added in large quantities to the model.

It is still yet a further object of the present invention to provide computer readable medium suitable for use in various computing system configurations that facilitate accomplishment of the foregoing objectives.

In accordance with the invention as embodied and broadly described herein, the foregoing and other objectives are achieved by providing methods and computer readable medium for ultimately developing an enlarged dosimetry plan for a treatment volume irradiated during radiation therapy with a photon, electron, or light-ion radiation source concentrated internally within a patient, or from an externally-applied radiation beam generated by a particle accelerator or some other means, such as a cobalt-60 radio-isotopic source. The dosimetry plan is available in "real-time" which especially enhances clinical use for in vivo applications. The real-time is achieved because of the novel geometric model construction of the treatment volume which in turn allows for rapid calculations to be performed for simulated movements of particles along particle tracks there through. The particles are exemplary representations of alpha, beta or gamma emissions emanating from a radiation source during various radiotherapies, such as brachytherapy, targeted radionuclides, or external beam teletherapy.

In a preferred embodiment, a medical image of a treatment volume irradiated during radiotherapy having a plurality of pixels of information is obtained. The pixels are: (i) converted into a plurality of substantially uniform volume elements having substantially the same shape and volume of the extended pixels; and (ii) arranged into a geometric model of the treatment volume. An anatomical material associated with each uniform volume element is defined and stored. Thereafter, a movement of a particle along a particle track is defined through the geometric model along a primary direction of movement that begins from the radiation source in a starting element of the uniform volume elements and traverses to a next element of the uniform volume elements. The particle movement along the particle track is effectuated in integer based increments until a position of intersection occurs that represents a condition where the anatomical material of the next element is substantially different from the anatomical material of the starting element. This position of intersection is then useful for indicating whether the particle has been captured, scattered or exited from the geometric model. From this intersection, a distribution of radiation doses can be enlarged from the actual radiation distributions represented in the medical image for use in various radiotherapies. The foregoing represents an advance in computational times by multiple factors of time magnitudes.

These and other objects and features of the present invention will become more fully apparent from the following description and appended claims, or may be learned by the practice of the invention as set forth hereinafter.

BRIEF DESCRIPTION OF THE DRAWINGS

In order to more fully understand the manner in which the above-recited and other advantages and objects of the invention are obtained, a more particular description of the invention will be rendered by reference to specific embodiments thereof which are illustrated in the appended drawings. Understanding that these drawings depict only typical embodiments of the invention and are not therefore to be considered to be limiting of its scope, the invention in its presently understood best mode for making and using the same will be described and explained with additional specificity and detail through the use of the accompanying drawings in which:

FIG. 2 is a flow diagram of the hierarchical operation for generating a dosimetry plan for radiotherapies having radiation sources concentrated internally within a patient;

FIG. 3 is a flow diagram for computationally escalating the radiation distribution of an irradiated treatment volume as invoked by the routine of FIG. 2 or, for an external radiation source;

FIG. 4 is a flow diagram for modeling the geometry of an irradiated treatment volume in accordance with the present invention;

DETAILED DESCRIPTION OF THE PREFERRED EMBODIMENTS

The present invention relates to methods and computer readable medium for ultimately developing an enlarged dosimetry plan for a treatment volume irradiated during radiation therapy with a radiation source concentrated internally within a patient or with an externally-applied radiation source. It is a feature of the present invention that this dosimetry plan is available in "real-time" which especially enhances clinical use for in vivo applications. The real-time is achieved because of the novel method of constructing the geometric model of the treatment volume which in turn allows for rapid calculations to be performed for simulated movements of particles along particle tracks there through. The particles are exemplary representations of alpha, beta or gamma emissions emanating from a radiation source during various radiotherapies, such as teletherapy, brachytherapy, or targeted radionuclides, but should not be construed as limited thereto.

In accordance with the present invention, diagrams are used herein to illustrate either the structure or processing of embodiments used to implement the system and method of the present invention. Using the diagrams in this manner to present the invention, however, should not be construed as limiting of its scope but merely as representative.

Figure 1:
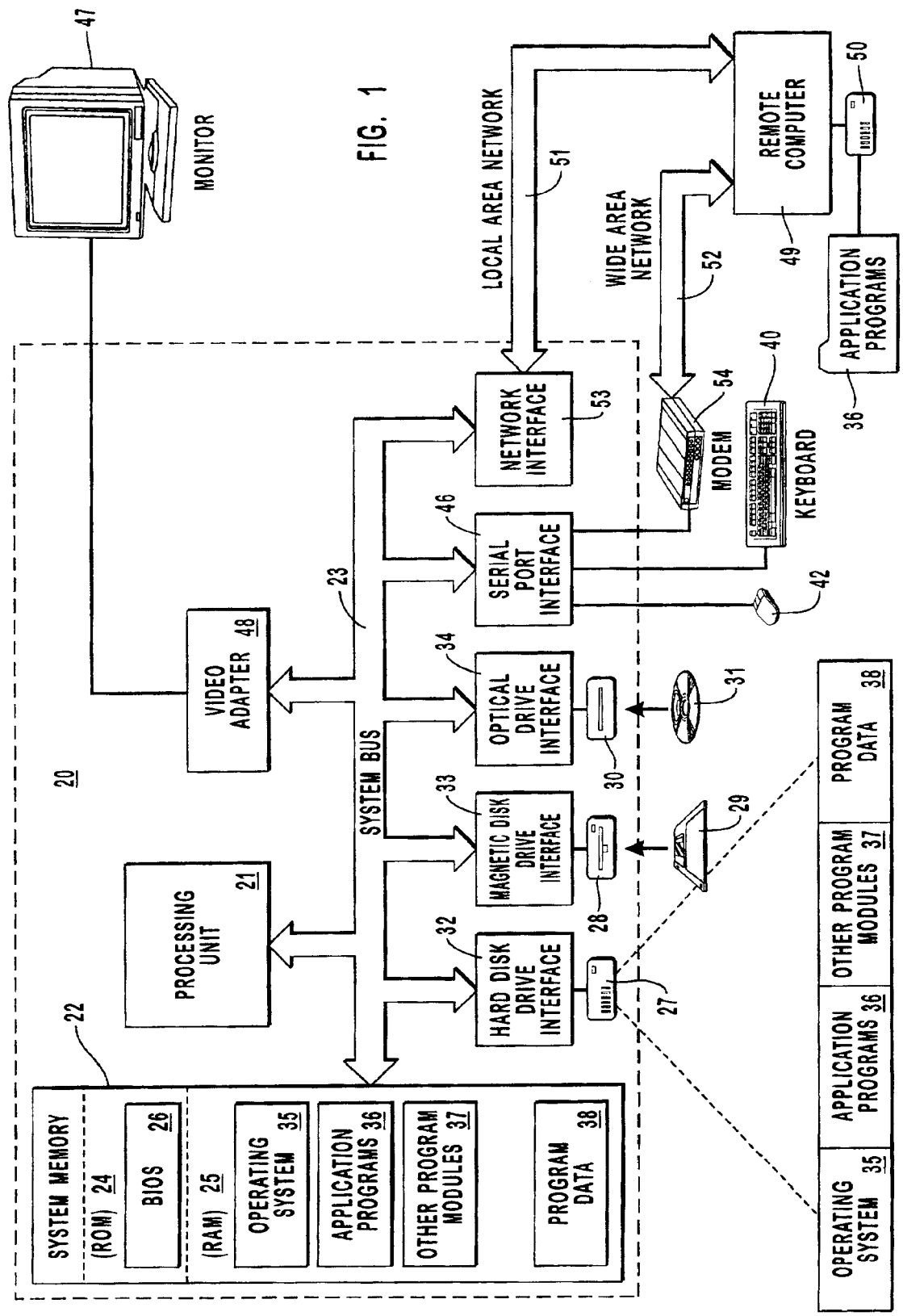
FIG. 1 is an exemplary system for providing a suitable operating environment for the present invention.

FIG. 1 and the following discussion are intended to provide a brief, general description of a suitable computing environment in which either the structure or processing of embodiments may be implemented. Since the following may be computer implemented, particular embodiments may range from computer executable instructions as part of computer readable media to hardware used in any or all of the following depicted structures. Implementation may additionally be combinations of hardware and computer executable instructions.

When described in the context of computer readable media having computer executable instructions stored thereon, it is denoted that the instructions include program modules, routines, programs, objects, components, data structures, etc. that perform particular tasks or implement particular abstract data types upon or within various structures of the computing environment. Executable instructions exemplarily comprise instructions and data which cause a general purpose computer, special purpose computer, or special purpose processing device to perform a certain function or group of functions.

The computer readable media can be any available media which can be accessed by a general purpose or special purpose computer. By way of example, and not limitation, such computer readable media can comprise RAM, ROM, EEPROM, CD-ROM or other optical disk storage, magnetic disk storage or other magnetic disk storage devices, or any other medium which can be used to store the desired executable instructions or data fields and which can be accessed by a general purpose or special purpose computer. Combinations of the above should also be included within the scope of computer readable media. For brevity, computer readable media having computer executable instructions may sometimes be referred to as "software" or "computer software."

With reference to FIG. 1, an exemplary system for implementing the invention includes a general purpose computing device in the form of a conventional computer 20. The computer 20 includes a processing unit 21, a system memory 22, and a system bus 23 that couples various system components including the system memory to the processing unit 21. The system bus 23 may be any of several types of bus structures including a memory bus or memory controller, a peripheral bus, and a local bus using any of a variety of bus architectures. The system memory includes read only memory (ROM) 24 and random access memory (RAM) 25. A basic input/output system (BIOS) 26, containing the basic routines that help to transfer information between elements within the computer 20, such as during start-up, may be stored in ROM 24. The computer 20 may also include a magnetic hard disk drive 27 for reading from and writing to a hard disk, not shown, a magnetic disk drive 28 for reading from or writing to a removable magnetic disk 29, and an optical disk drive 30 for reading from or writing to removable optical disk 31 such as a CD-ROM or other optical media. The hard disk drive 27, magnetic disk drive 28, and optical disk drive 30 are connected to the system bus 23 by a hard disk drive interface 32, a magnetic disk drive-interface 33, and an optical drive interface 34, respectively. The drives and their associated computer-readable media provide nonvolatile storage of computer readable instructions, data structures, program modules and other data for the computer 20.

Although the exemplary environment described herein employs a hard disk, a removable magnetic disk 29 and a removable optical disk 31, it should be appreciated by those skilled in the art that other types of computer readable media which can store data accessible by a computer include magnetic cassettes, flash memory cards, digital video disks, removable disks, Bernoulli cartridges, random access memories (RAMs), read only memories (ROM), and the like.

Other storage devices are also contemplated as available to the exemplary computing system. Such storage devices may comprise any number or type of storage media including, but not limited to, high-end, high-throughput magnetic disks, one or more normal disks, optical disks, jukeboxes of optical disks, tape silos, and/or collections of tapes or other storage devices that are stored off-line. In general, however, the various storage devices may be partitioned into two basic categories. The first category is local storage which contains information that is locally available to the computer system. The second category is remote storage which includes any type of storage device that contains information that is not locally available to a computer system. While the line between these two categories of devices may not be well defined, in general, local storage has a relatively quick access time and is used to store frequently accessed data, while remote storage has a much longer access time and is used to store data that is accessed less frequently. The capacity of remote storage is also typically an order of magnitude larger than the capacity of local storage.

A number of program modules may be stored on the hard disk, magnetic disk 29, optical disk 31, ROM 24 or RAM 25, including an operating system 35, one or more application programs 36, other program modules 37, and program data 38. Such application programs may include, but are not limited to, random generation modules, such as Monte Carlo simulators and graphic modules or modeling modules for generating graphics and models for user display. A user may enter commands and information into the computer 20 through input devices such as a keyboard 40 and pointing device 42. Other input devices (not shown) may include a microphone, joy stick, game pad, satellite dish, scanner, or the like. These and other input devices are often connected to the processing unit 21 through a serial port interface 46 that is coupled to system bus 23, but may be connected by other interfaces, such as a parallel port, game port or a universal serial bus (USB). A monitor 47 or other type of display device is also connected to system bus 23 via an interface, such as video adapter 48. In addition to the monitor, computers often include other peripheral output devices (not shown), such as speakers and printers. Scanner peripheral devices (not shown) for reading data, imagery, graphics or other information into the computer are often also included.

The computer 20 may operate in a networked environment using logical connections to one or more other computing configurations, such as remote computer 49. Remote computer 49 may be a personal computer, a server, a router, a network PC, a peer device or other common network node, and typically includes many or all of the elements described above relative to the computer 20, although only a memory storage device 50 has been illustrated in FIG. 1. The logical connections depicted in FIG. 1 between the computer 20 and the remote computer 49 include a local area network (LAN) 51 and a wide area network (WAN) 52 that are presented here by way of example and not limitation. Such networking environments are commonplace in offices enterprising wide computer networks, intranets and the Internet.

When used in a LAN networking environment, the computer 20 is connected to the local network 51 through a network interface or adapter 53. When used in a WAN networking environment, the computer 20 typically includes a modem 54 or other means for establishing communications over the wide area network 52, such as the Internet. The modem 54, which may be internal or external, is connected to the system bus 23 via the serial port interface 46. In a networked environment, program modules depicted relative to the computer 20, or portions thereof, may be stored in the local or remote memory storage devices and may be linked to various processing devices for performing certain tasks. It will be appreciated that the network connections shown are exemplary and other means of establishing a communications link between the computers may be used.

Moreover, those skilled in the art will appreciate that the invention may be practiced with other computer system configurations, including hand-held devices, multiprocessor systems, microprocessor-based or programmable consumer electronics, network PCs, minicomputers, computer clusters, mainframe computers, and the like.

With reference to FIG. 2, a flow diagram of the overall hierarchy of generating a dosimetry plan for radiotherapies having radiation sources essentially concentrated internally within a patient is depicted generally as 100.

At step 102, a radiation source is administered or introduced substantially within a patient. In general, this step is well known and includes temporary or permanent administration of radiation sources during radiotherapies such as targeted radionuclides and brachytherapy and may be injected, implanted, ingested, combinations thereof or by any other means of administering a radiation source to a patient. The radiation source is also generally well known and includes sources such as radium, radioactive isotopes of elements and/or compounds such as radioactive gold, Au-198, iodine-125, iridium-192, palladium-103, ytterbium-169, which are all common in the treatment of prostate cancer, for example, or any other element or compound capable of emitting or reacting to emit alpha, beta or gamma emissions. In general, the area of the patient where the radiation source is designated to irradiate during use is defined as the treatment volume or a portion of the treatment volume.

In a preferred embodiment, the radiation source is introduced in concentrations or amounts smaller than required to conformally irradiate the treatment volume, yet large enough to be observed so as to obtain data or information on the irradiation. In this manner, whatever radiation distribution the radiation source emits, the radiation distribution can be enlarged for purposes of follow-up planning, escalating dosage, performing additional treatment or for any other reason.

At step 104, as the radiation source emanates, the radiation distribution is imaged by means well known in the art. By way of example and not limitation, some preferred imaging means include CT scanning, radionuclide scanning, MRI scanning, PET scanning, gamma cameras, ultrasound or by similarly related or unrelated means.

At step 106, the radiation distribution actual imaged is computationally escalated or enlarged. In this manner, since the radiation source is known and actual irradiation of the treatment volume in a patient is actually observed, the computational dosimetry for an enlarged area, for purposes of escalating dosage, for example, is dramatically improved.

Some of the advantages realized by this method include, but are not limited to: (i) providing escalated dosimetry as a function of actual radiation distributions in a patient under examination; (ii) using all available information; and (iii) increasing accuracy by using the actual radiation sources instead of modeled sources.

Thereafter, once the radiation distribution has been computationally escalated, the actual radiation source can be increased in dosage or supplanted with an enlarged dosage and the steps repeated to achieve improved radiation results. This step is indicated by the dashed between steps 106 and 102.

With reference to FIG. 3, the step 106 of computationally escalating the radiation distribution is accomplished as a two-step process. At step 110, the imagery of the radiation distribution of the treatment volume and of the surrounding vicinity obtained from the administered radiation source is modeled. Then, at step 112, particle transport through the model can be calculated to escalate the radiation distribution from the irradiated treatment volume. Preferably, the particles are exemplary representations of alpha, beta or gamma emissions emanating from the radiation source during various radiotherapies involving internal radiation sources, such as brachytherapy or targeted radionuclides, but should not be construed as limited thereto. Accordingly, FIG. 3 indicates alternative embodiments of the process to computationally escalate the radiation distribution. In one embodiment, indicated by steps 110 and 112, an internal radiation source such as an emitter is employed. In an alternative embodiment, indicated by steps 113 and 112, a directly applied external radiation beam is employed.

With reference to FIG. 4, a flow diagram for modeling imagery of the radiation distribution (step 110) in accordance with the present invention comprises the steps of: (i) converting pixels to "univels," step 140; and (ii) mapping univels to an array, step 142.

It should be appreciated that medical imagery is generated and obtained from numerous and diverse sources, such as CT, MRI and PET. In general, these sources generate an image of a structure by making a series of plane cross-sectional slices along a common axis. Some of these sources provide resolutions of 256×256 pixels of information by about 40 axial slices, such as with CT. Some have finer resolution like 512×512 pixels of information by about 512 axial slices.

Since these sources provide the medical imagery in the form of pixels of information, it is a feature of this invention to directly convert these pixels into "elements" from which a geometric model can be produced. Preferably, these elements are of the substantially same shape and volume as the pixel of information. In this manner, valuable time in configuring the geometric model is preserved and no loss of accuracy is introduced because of the direct one-to-one correspondence between a pixel of information and the modeling element. As used herein, these elements are referred to as uniform volume elements or "univels" and are proportional representations of the pixels they represent. Other attributes include a substantially uniform volume as between all elements.

It should be appreciated, that pixels of information as used herein also broadly represents any digitizing or numerical representations or any other means of indicating discrete or substantially discrete units of information obtained from the medical imaging source.

Since typical medical imagery provides pixels in about 1 mm×1 mm×5 mm right parallelepipeds, the preferred univels have this same shape and volume. The conversion from pixels to univels can efficaciously be accomplished with a pixel paint program or a filling between non-uniform rational B-spline (NURBS) surfaces. Once converted, and given the foregoing dimensions of medical imagery, a computer would need only approximately 2.6 MB of storage space for a 256×256×40 medical image set and 134 MB of storage space for a 512×512×512 medical image set. Although 134 MB of storage space is relatively large, this is quite affordable given the configurations of computing systems presently used.

Inherent with a pixel of information in a medical image is an anatomical material, such as bone, soft tissue, blood, etc or the radiation source itself administered at step 102. Such materials are broad ranging and are often identified with bytes of information. Whatever the anatomical material, each univel is associated with a material and is mapped to an array or simply stored at step 142.

Figure 5A:
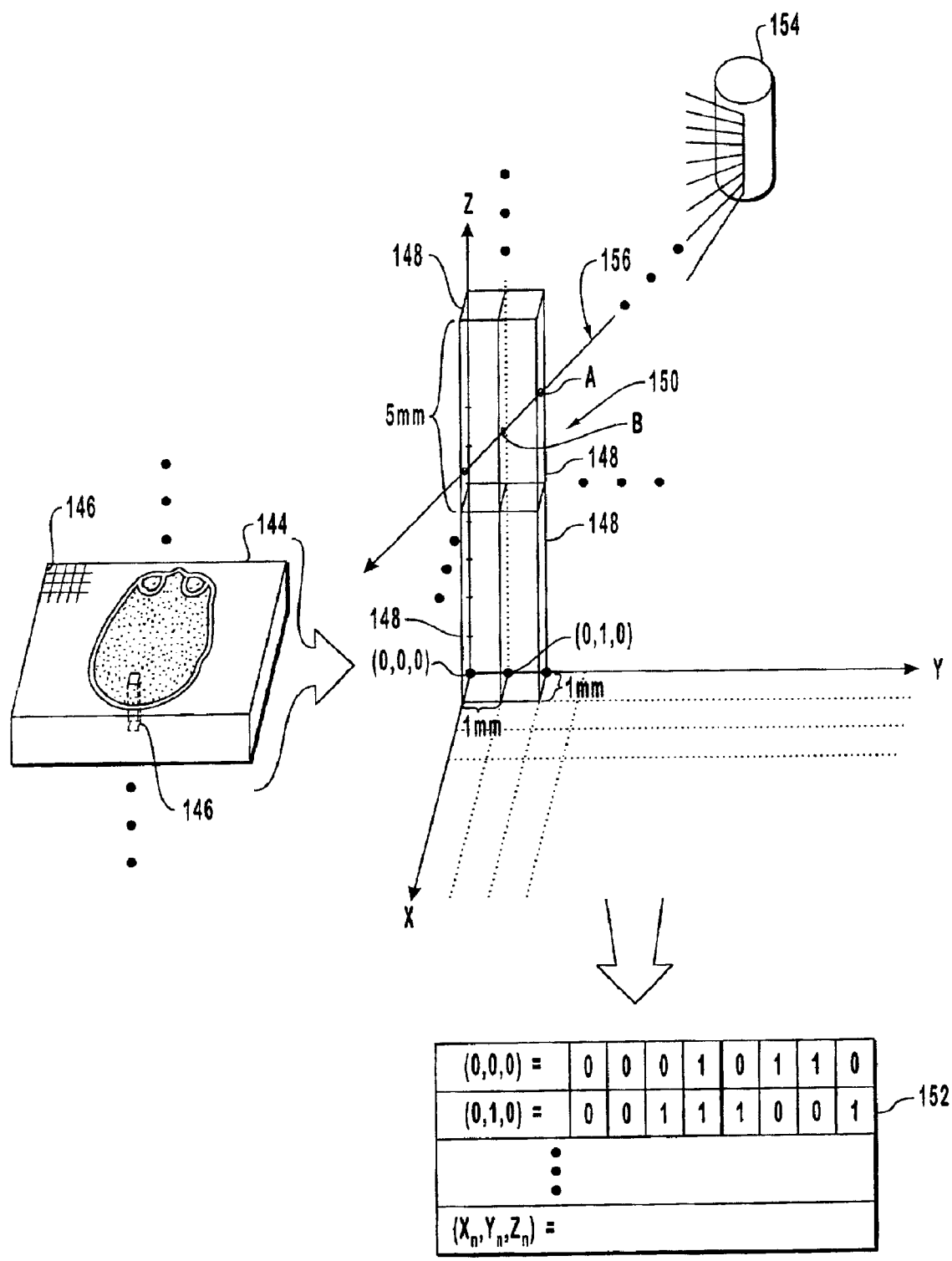
FIG. 5A is an exemplary diagram for converting pixels of medical imagery into a geometric model and for mapping the pixels into an array of anatomical materials in accordance with the present invention.

A diagram of the foregoing modeling of imagery is illustrated with reference to FIG. 5A. In FIG. 5A, a singular axial slice 144 representative of any of a variety of cross-sectional slices from a medical image is depicted as having a plurality of pixels 146. For clarity of the illustration, only a small portion of the pixels are shown with only one pixel being shown near the central portion of the axial slice 144. The pixels 146 are converted into a plurality of univels 148. In this embodiment, each univel 148 is typically about 1 mm×1 mm×5 mm respectively along the X-, Y- and Z-axes.

Since each axial slice 144 is part of a larger medical image, as indicated by ellipses, each pixel 146 of each axial slice 144 is converted into univels 148 which, in turn, are stacked into a geometric model 150 of the treatment volume irradiated after administration of the radiation source during the radiation therapy. In this embodiment, the geometric model 150 is represented by four univels 148 (two univels beneath two univels) but it should be appreciated that the univels extend outward in each of the X, Y and Z directions as indicated by ellipses. It should also be appreciated that the model 150 may be represented by geometric shapes as indicated in the figure, by mathematical equations or computer executable instructions representative of the shapes or by similarly related means.

As used herein, "geometric model," "pixel of information," "anatomical material" and "treatment volume" may alternatively be referred to as a "model," "pixel," "material" or "irradiation volume," respectively. These alternative forms are useful for brevity or because of their common association amongst those skilled in the art.

Once the univels are mathematically stacked into the geometric model of the treatment volume, the anatomical materials represented by the univels are mapped to an array 152. Many mapping schemes are available and in this embodiment, a useful scheme uses a corner coordinate of each univel to identify the anatomical material thereof. For example, corner coordinate (0,0,0), corresponding to the X, Y and Z axes of the illustrated Cartesian coordinate system, is mapped to a binary representation of the number 22. The corner coordinate (0,1,0) is mapped to a binary representation of the is number 57. These numbers preferably correspond to a look up table stored as part of the computing system configuration as part of either the local or remote storage devices. Thus, it should be appreciated that at least 256 different representations of anatomical materials or radiation sources can be represented in this embodiment. In this embodiment, 22=scalp and 57=skull and other number representations are available for various other anatomical materials. This mapping continues until all anatomical materials of the univels have been mapped illustrated by ellipses continuing to corner coordinates $(X_n, Y_n, Z_n)$. This mapping, however, should not be construed as limiting. For example, the mapping could occur to a centered coordinate of each univel or any other useful scheme. Moreover, the described Cartesian coordinate system could be replaced with other coordinate systems such as a vector magnitude/angle coordinate systems, e.g., $(r,\theta)$, and still maintain its usefulness. The foregoing mapping schemes and coordinate systems are exemplary and should not be construed as limiting.

By geometrically modeling the treatment area in this manner, it should be appreciated that the following advantages are realized over the prior art: (i) numerous anatomical materials are represented by the geometric model which ultimately improves radiation dosage accuracy; (ii) no loss of accuracy in modeling is introduced because of the one-to-one correspondence with the medical image pixels; (iii) time is preserved during the modeling because no intermediate steps are required to correlate pluralities of pixels to the elements used to geometrically model the treatment volume; (iv) any pertinent medical imagery can be accurately modeled without restriction; and (iv) all known information is utilized when computing dosimetry plans for clinical or research use. Yet, the foregoing is merely representative of some of the advantages.

Once the geometric model 150 is generated and the anatomical material of the univels are mapped, simulated transports or movements of "particles" are tracked or followed through the geometric model to ascertain, among other things, how alpha, beta or gamma emissions would travel through the model. Ultimately, this tracking leads to a representative distribution of radiation doses, as is known, useful during the radiotherapy. As described herein, the particles emanate from a radiation source 154.

Figure 5B:
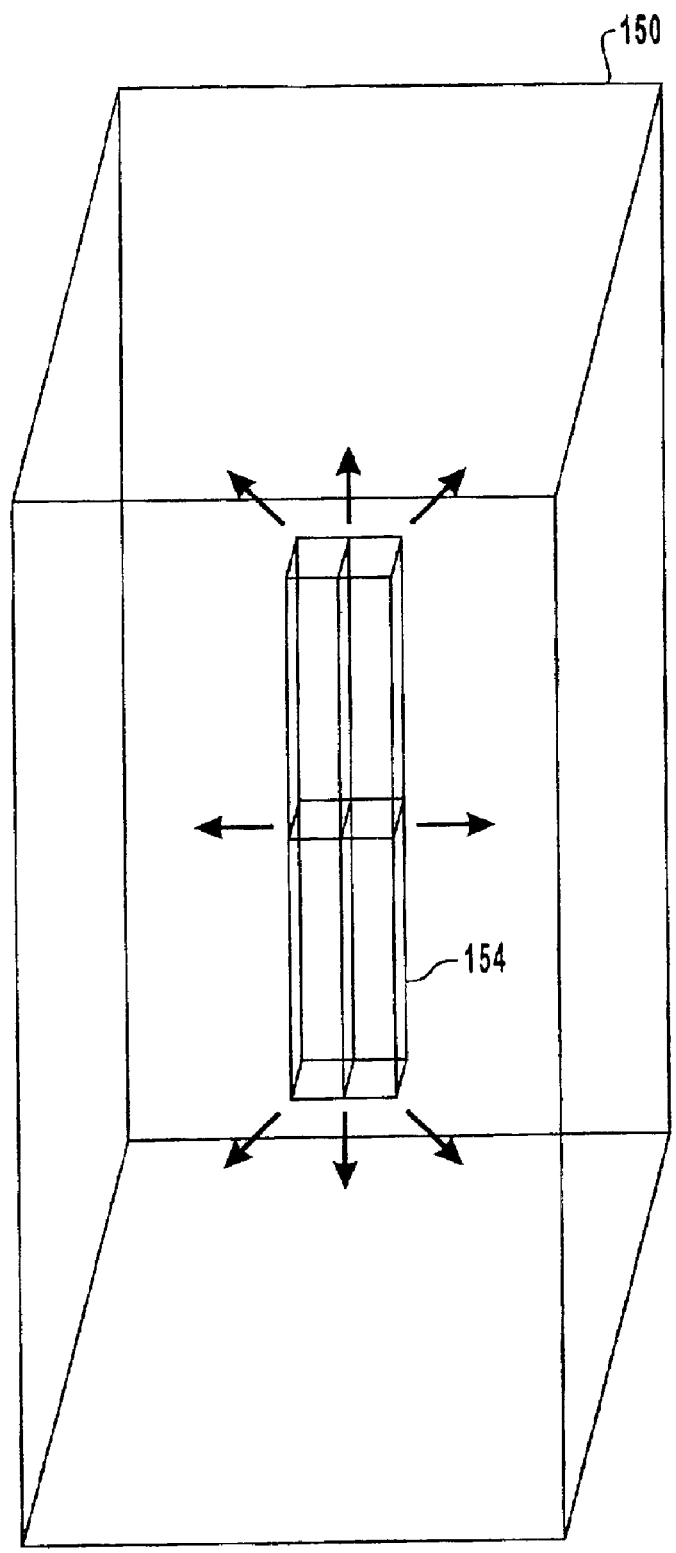
FIG. 5B is a diagram of a geometric model having a radiation source concentrated internally therein.

It should be appreciated that although radiation source 154 is illustrated as removed from the univels 148 of the model 150, the radiation source is actually concentrated internally within a patient in this illustrative example. Thus, with reference to FIG. 5B, the radiation source 154 is depicted as one or more of the univels and is concentrated internally within model 150. The actual compound of the radiation source is correspondingly mapped in array 152. Alternatively, the radiation source may be selected from an externally-applied beam, described as a planar boundary condition rather than as an internal volumetric source within a univel.

As depicted in FIG. 5A, radiation emissions emanating from radiation source 154 are identified by particle track 156. Preferably, the particular particle track followed by a particle is selected as a multi-dimensional probability distribution function based on a series of machine-generated pseudo numbers generated in a well known manner by Monte Carlo simulation.

In general, the particle leaves the univel of the radiation source, or, alternatively, the planar boundary where an external source is described, along particle track 156 and enters an adjacent univel or starting element of the univels at point A. From position A, in the case of an internal source, the particle traverses through the univel into a next univel at position B. From position B, the particle traverses from the previous univel into the next element of the univels and continues until either the particle exits from the geometric model or is captured by the anatomical material of the univel. For an external source, the particle travels from the planar source on the model boundary until it encounters the first univel in its path on the surface of the anatomical geometry. The particle then enters this univel, and then proceeds as if it had been born within this univel, as in the case of an internal source.

It should be appreciated, however, that although the particle is described as traversing along the particle track, the particle transport through the model is preferably just a simulation of how a particle would travel through the model during therapy. The simulation is preferably effectuated by means of computer executable instructions on a medium input to the computing system configuration described in the context of the exemplary operating environment. Thus, the particle movement along the particle track, as described herein, may be either a simulated or an actual movement.

Figure 6A:
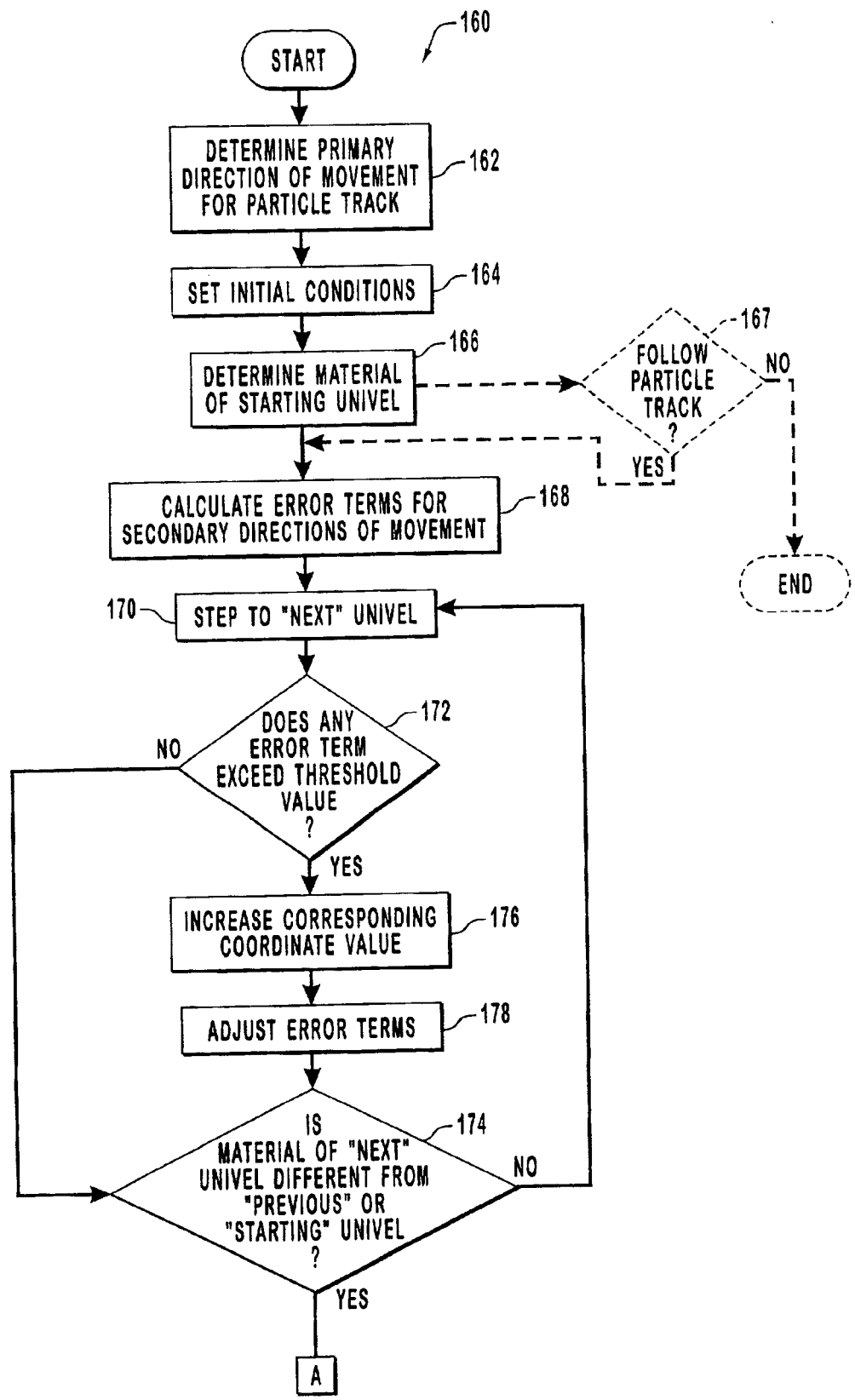
FIG. 6A is a first portion of a flow diagram for calculating particle transport simulations through a geometric model of a planned irradiation volume in accordance with the present invention.
Figure 6B:
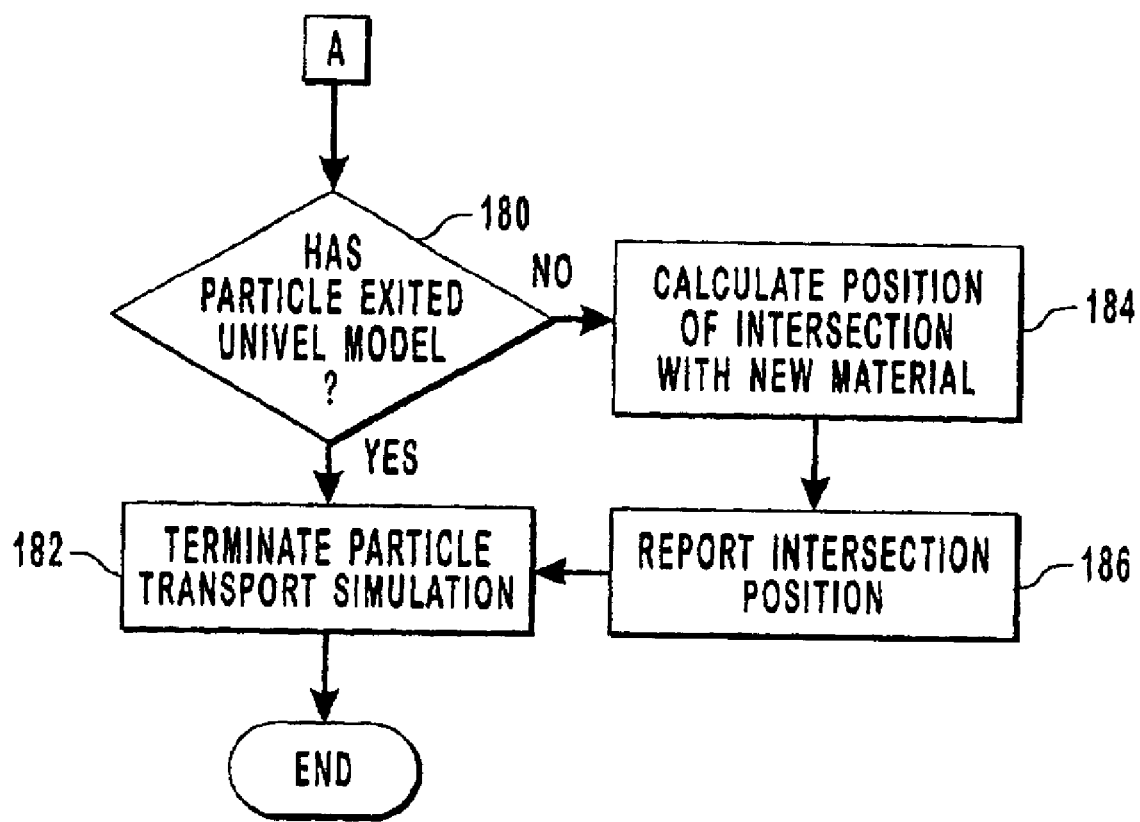
FIG. 6B is a second portion of a flow diagram for calculating particle transport simulations through a geometric model of a planned irradiation volume in accordance with the present invention.

With reference to FIGS. 6A and 6B, a method for tracking a singular particle through the geometric model 150 until the particle is exited or intersected with a new material, i.e., absorbed or scattered, is depicted generally as 160. It should be appreciated that this method is repeated numerous times for numerous particles.

The calculations for simulated particles transported through a model begin with an initial position and velocity vector. This step is assumed as given for the following discussion. As another given, it is assumed that the initial position of the particle movement along the particle track is within the starting element of the univels (hereinafter starting univel). Preferably, the starting univel is adjacent the univel of the radiation source.

At step 162, no matter which univel is the starting univel, a primary direction of movement for the particle along the particle track is determined from which a set of initial conditions can be established 164. Setting initial conditions once will later enable the quick and efficacious tracking of a movement of the particle through the geometric model. To further illustrate this, in FIG. 7, an exemplary particle track is depicted in three dimensions of a Cartesian coordinate system as particle track 200. The particle track 200 is depicted in two dimensions, in the X-Y plane, as particle track 202. From this illustration, it is seen that the track advances in the greatest intervals in the positive Y direction of travel. Thus, the primary direction of movement is in the positive Y direction and the initial conditions will be established in accordance with this positive Y direction. Whatever other directions of movement remain, here the X and Z directions, are termed the secondary and tertiary directions of movement, or vice versa depending upon how classified.

From the figure, the initial Y coordinate is $y_0=1.8$, which is somewhere in the starting univel, and the initial X and Z coordinates, $x_0$ and $z_0$, are some values along the particle track. The next step in setting the initial condition is to create a center value coordinate in the primary direction of movement. Centering is done to ensure that the particle track is sampled at representative points, of which, the center is more representative than either end. This is done by choosing the center value between integer values. Thus, since $y_0=1.8$, y is between integers 1 and 2, such that: $1 \leq y_0 < 2$, the center value is 1.5. This center value is a portion of the adjusted coordinate from which the particle movement along the particle track will begin and is designated as $y_1=1.5$. The values for the X and Z directions are needed to represent the entire adjusted coordinate.

Since the particle track 200 is a straight line, the line is merely extended to the adjusted coordinate as indicated by dashed line 204 in the both three and two dimensions. With $y_1=1.5$ as given, $x_1$ and $z_1$ are computed. From FIG. 7, it can be read that $x_1=3.5$ and $z_1=5.6$. Such coordinates are logged in table 210 in FIG. 7.

Figure 7:
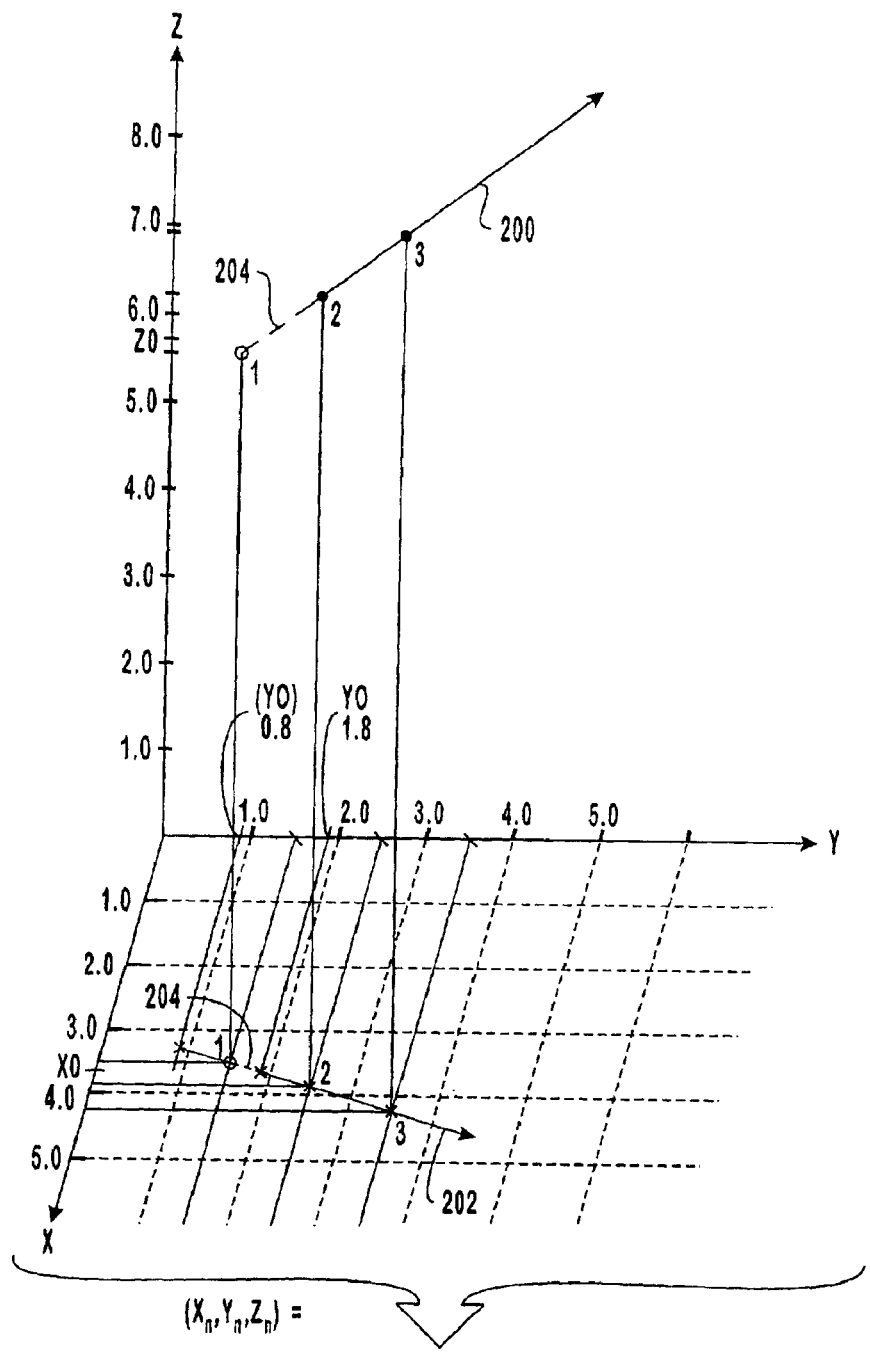
FIG. 7 is an exemplary diagram for depicting the primary direction of movement of a particle track, for setting the initial conditions and for stepping through univels during particle transport simulations as invoked by the routines of FIGS. 6A and 6B.

Thereafter, in FIG. 6A at step 166, the anatomical material of the starting univel is determined by reading the anatomical material from the array. Since, the array was mapped using integers, the anatomical material of the starting univel is easily determined by rounding each of the coordinates ($x_1,y_1,z_1$) down to the nearest integer. As such, for (3.5, 1.5, 5.6) the starting material of that univel is found in the array at (3,1,5) as illustrated in table 210 (FIG. 7).

Perhaps not readily apparent, the advantage of this is found as a result of the way computing system configurations perform calculations. For example, although a computer could determine the anatomical material of the univel from the coordinates (3.5, 1.5, 5.6) it is easier and much faster for a computer if floating point mathematics is not involved when computing and storing. Thus, by determining the anatomical material of the univels with integers, valuable computational time is preserved for other calculations and clinical uses.

Alternatively, it should be appreciated that the same center coordinates could be selected if, for example, the initial Y coordinate is $y_0=0.8$. Then, since $y_0=0.8$, the two nearest values centered in a univel along the Y axis are y=0.5 and y=1.5. If the primary direction of movement for the particle track was directed negatively along Y, then $y_1=0.5$ would be used. Since the particle track is positively directed, however, $y_1=1.5$ is the first centered value in the primary direction of movement. Again, with an extension of the particle track, the initial x, and z, coordinates can be read.

It should also be appreciated that an alternative method of determining the anatomical material of the starting univel could also be accomplished by using an integer floor or ceiling value of the univel containing the initial point. With this alternative, it is even within the scoop of the present invention that steps 162 and 164 could be interposed such that the anatomical material of the starting univel is determined before setting the initial conditions.

As the particle is tracked, it is evident that coordinates corresponding to the secondary and tertiary directions of movement will need to be updated as the primary (Y)

coordinate is tracked in integer based increments. Since the secondary and tertiary directions of movement are treated in the same manner, they will be described hereinafter as secondary directions of movement. Thus, at step 168, error terms are calculated for the secondary directions of movement to keep track of when either should be independently incremented. Preferably this adjustment occurs if either exceeds a predetermined threshold.

Thereafter, at step 170, the movement of the particle track is traversed in integer based increments along the primary direction of movement into the "next" univel. In this context, this traversal is also referred to as a "step" since it occurs in integer based increments.

Thus, with reference to the table 210 (FIG. 7), the traversal of the particle along the particle track steps in the Y direction according to $y_1=1.5$, $y_2=2.5$, $y_3=3.5$ until the ending element of the univels is reached where $y=y_n$. Although the integer steps are described herein as positive 1, it should be appreciated that the integers can be negative and can be in other logical values. It should also be appreciated that the integer values that are stored need not correspond to centered values along the primary direction of movement. It is just that the centered values provide the most representative sampling along the particle track.

Having stepped to a "next" univel at step 170, it is determined, at step 172, whether any of the error terms exceed the threshold value. If the error terms do not exceed the threshold values, a determination about the anatomical material of the next univel is made at step 174 to see if it is different from the previous or starting univel. Again, this is simply done by using the stored integer position values to examine the anatomical material mapped in array 152 for that univel against the previous univel. The actual points examined are expressed as floats but are only kept track of as integers. Thus, as in table 210 (FIG. 7), for the next univel having coordinates of (3.83, 2.5, 6.26) the anatomical material for that univel is stored in the array at (3,2,6) and a comparison between anatomical materials is made against (3,1,5). Similarly, for the univel having coordinates (4.13, 3.5, 6.93) the anatomical material for that univel is stored in the array at (4,3,6).

Because of the eventual possibility that stepping in the primary direction of movement without stepping along the particle track in the secondary direction of movement will cause an error in determining the anatomical material of the univel under examination, at step 172, if the error term exceeds the threshold value, an increase in the corresponding coordinate value is performed (step 176) to ensure the proper univel is being examined. Thereafter, at step 178, an adjustment of the error terms is performed to account for the increase in the corresponding coordinate value. Although not shown, the error term could also be adjusted to indicate that stepping only occurred in the primary direction of movement. Thence, once adjusted, the determination of the anatomical material of the next univel is made at step 174.

It should be appreciated that the anatomical material of the "next" univel is made in comparison to the starting univel, or, as the movement of the particle is tracked along the particle track, is made in comparison to the previous univel. If, at step 174, the anatomical material is not at least substantially different, the movement of the particle along the particle track is reiteratively traversed to the next univel (step 170) until eventually the particle exits the geometry or intersects with a new material.

Thus, at step 174, if the anatomical material of the next univel is different from the previous or starting univel, a determination is made, at step 180, to see if the particle has exited the geometric model. As in the prior art, if the particle has exited the geometric model, the particle transport simulation is terminated at step 182.

If the particle has not exited the geometric model at step 180 and the anatomical material of the next univel is different from the previous univel, the position of intersection with the new material is determined at step 184. When determined, this position of intersection is reported at step 186 for use in another part of the computer executable instructions.

It should be appreciated from the foregoing that computational time is greatly preserved by stepping through the geometric model in integer based increments because each of the stepping computations and each determination about the anatomical material of each univel is performed by the computer without requiring the use of floating point mathematics. Thus, a medical image having pixels of information in 512×512 resolution×512 axial slices, millions of computations are performed over the course of numerous particles emanated from a radiation source. As described subsequently, this reduction in tracking time has been shown to be at least one order of magnitude faster than any computations heretofore known in the field.

Figure 8:
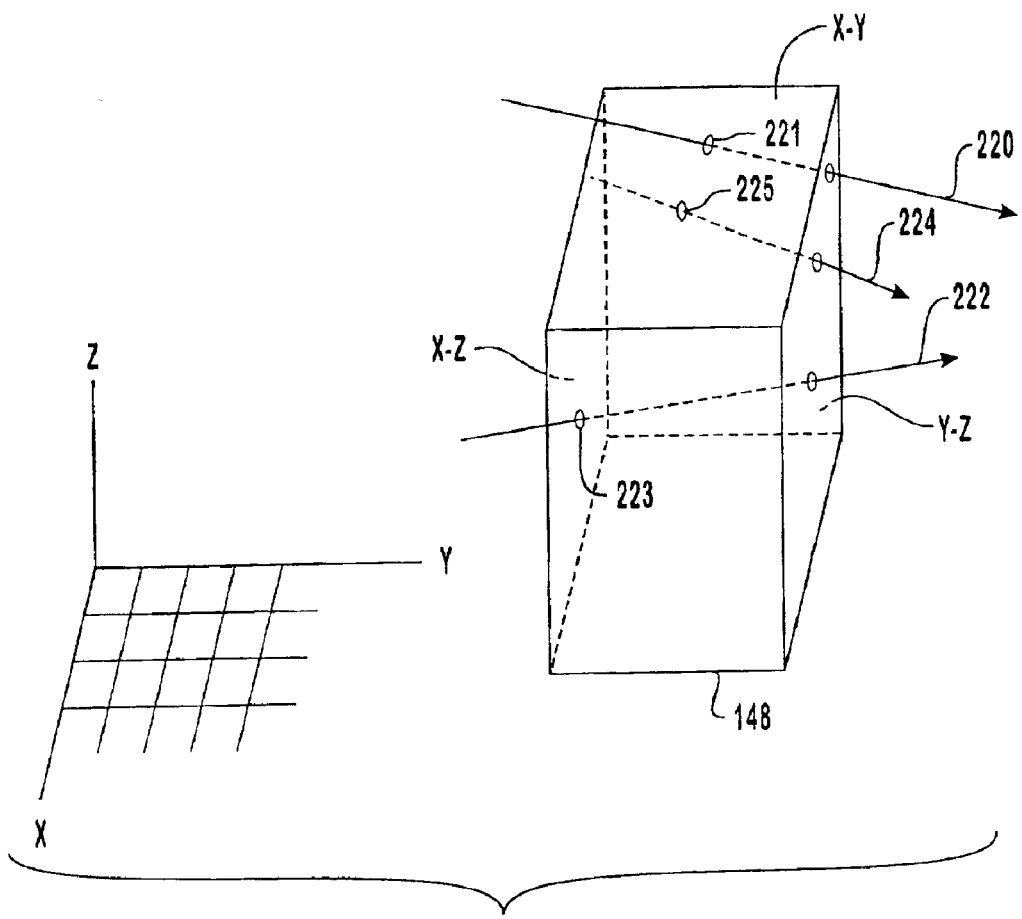
FIG. 8 is a diagram useful in describing the calculation of an intersection position along a particle track between various anatomical materials as invoked by the routines of FIGS. 6A and 6B.

The step 184 for determining where the position of intersection with the new material happens, is further described with reference to FIGS. 8 and 9. In FIG. 8, it is known that in some univel 148, the particle traveling along the particle track entered an anatomical material different from the previous univel. To determine the precise intersection, it is first known that the particle entered the univel 148 along the particle track through one of three planes. The particle may have entered the univel: through the X-Y plane as along particle track 220; through the X-Z plane along particle track 222; or through the Y-Z plane along particle track 224. The X, Y and Z planes being taken in reference to the Cartesian coordinate system depicted. Again, other coordinate systems can be used.

Figure 9:
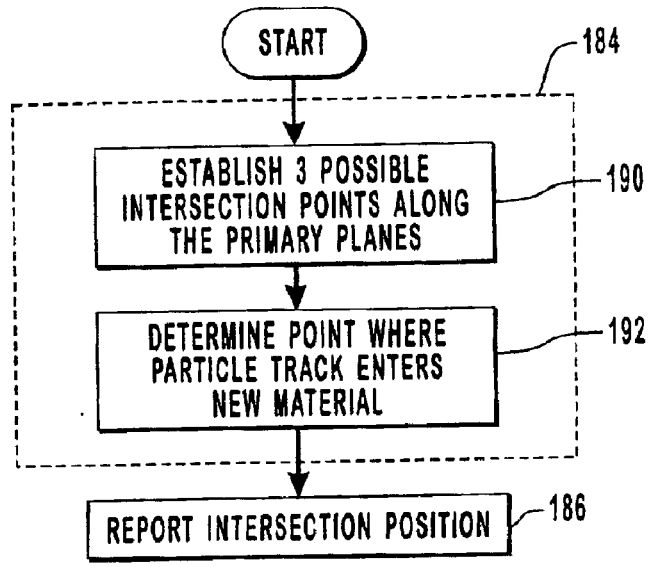
FIG. 9 is a flow diagram for calculating an intersection position between various anatomical materials as invoked by the routines of FIGS. 6A and 6B.

In a preferred embodiment, with reference to FIG. 9, three possible intersection points are established along the three primary planes described above, step 190. For example, the first position is 221 along particle track 220. The second position is 223 along particle track 222. The third position is 225 along particle track 224. Since each of these three positions are along a planar surface of a univel, a small epsilon may be added to move each of the three positions inside the univel by a small amount so that ambiguity of being on the planar surface can be avoided for computational purposes.

In a preferred embodiment, the three positions correspond to a floor or ceiling operator. The floor or ceiling is in reference to whether the particle track is moving in positive or negative increments. If positive, a floor is set. If negative, a ceiling is set. An example of this is depicted by particle track 222 in which positive increment advancement occurs in the Y and Z directions and negative increment advancement occurs in the X direction. Then, at step 192, the position where the particle track first enters the new material is determined. This is done by examining whichever particle through one of the three positions first hits or intersects the anatomical material that is different from the previous univel, this is the position of intersection. Again, this intersection position is reported at step 186. Floor and ceiling operators are well known in the art and are not described herein in detail.

Figure 10:
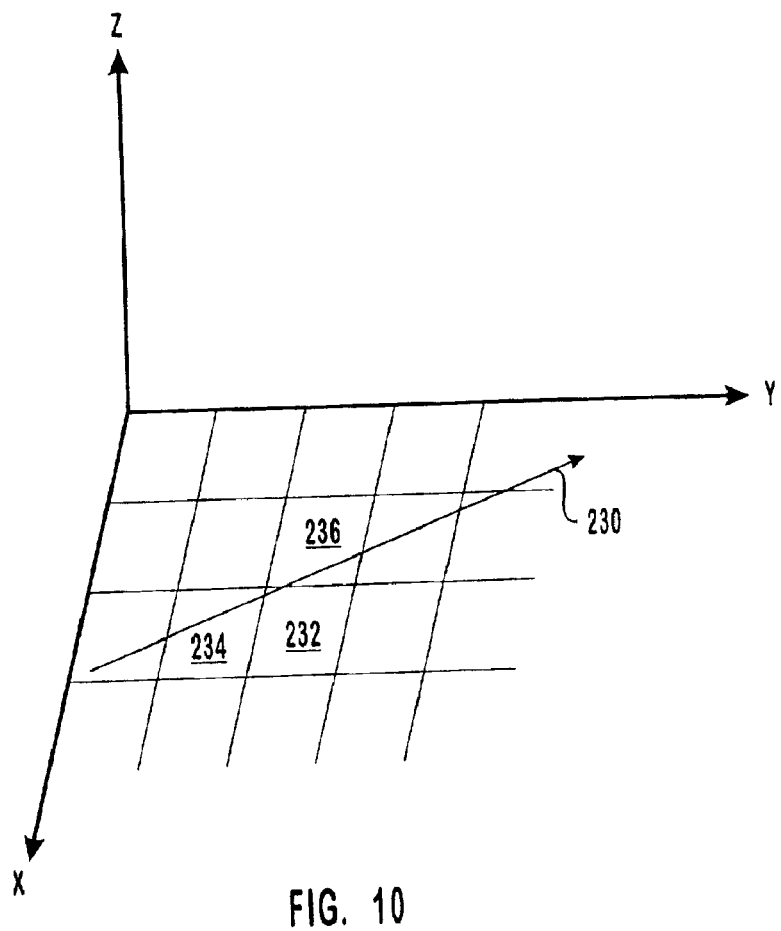
FIG. 10 is a diagram of a skipped univel in accordance with a preferred embodiment of the present invention.

With this method of integer based tracking of a movement of a particle along a particle track through a geometric model, it should be appreciated that some univels may be skipped over when tracking the particle. An example of this is shown with reference to FIG. 10, wherein a particle track 230, shown only in the X-Y plane, traverses through a small corner of univel 232. As such, if univel 232 is of the same anatomical material as univel 234, there is no need to perform a detailed examination regarding this univel and progression of the particle track can continue to univel 236. Thus, it is only when a univel has a different anatomical material from the previous univel that any further detailed calculations are required to be made. If the anatomical material of univel 232 is different, but the particle track reenters the original material in univel 236, then an insufficient volume in 234 was intersected to count as a boundary crossing. In the case where the anatomical material of 236 is different than 234, univel 232 will also be examined when determining the precise crossing into the new material since three planes of entry into the new material are considered. Again, when calculations for particle tracks are performed through millions of univels, tremendous computational time is saved.

In contrast to the prior art, it should be appreciated that computational accuracy is improved with more representations of the treatment volume than with fewer. For example, some methods in the prior art used 500 pixels as a single element representation for tracking a particle movement. Yet, in a 256×256 resolution, this only equates to about 130 elements in the model. If a particular particle track only passed through a small portion of these 130 elements, an accurate understanding required for computational dosimetry would be severely lacking. Yet here, a 256×256 resolution equates to 65,536 univels per axial slice. But because the tracking is performed in integer based increments, the tracking is not only faster but yields more accurate data in the dosimetry planning.

In an alternate embodiment, after step 166 (FIG. 6A), a decision 167 is made whether to follow along the particle track or not. When performing Monte Carlo simulation using an alternative scheme known as "boundary elimination," it is only necessary to know the material of the starting univel and not required to follow along the particle track to determine the next material intersection. Thus, for this alternate method, and for some editing purposes, return is made to the calling program immediately after determining the material of the starting univel. As such, this alternative step is indicated by dashed lines.

Figure 11:
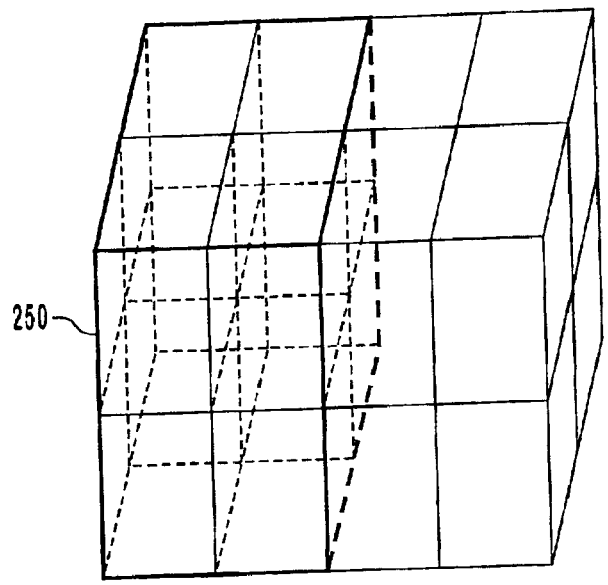
FIG. 11 is a diagram of a univel useful in calculating particle transport simulations through a geometric model when provided medical imagery has very fine resolution capabilities in accordance with an alternative embodiment of the present invention.

With reference to FIG. 11, it should be appreciated that as medical imagery becomes even more sophisticated, it is expected that even greater resolutions will be provided, such as in a 1000 pixel×1000 pixel resolution with 1000 axial slices. Thus, to improve computational times for tracking a particle movement through the geometric model, groupings of elements may be advantageously arranged. One such grouping uses a super univel 250 comprised of an arrangement of smaller univels in a 2×2×2 configuration. Still other combinations of univels can be effectuated.

EXAMPLE 1

The following represents data obtained from tracking a movement of 100,000 particles along random particle tracks (Monte Carlo simulated) through a geometric model constructed from a 256×256×medical image consisting of a buffer material, scalp, skull, brain and tumor anatomical materials.

The particle tracks began at a random initial position in the geometric model and traversed in a random direction. Each movement was tracked along the particle track until either the particle intersected an anatomical material different from the anatomical material of the previous univel or was exited from the geometric model. Of the 100,000 particle tracks, 55,137 positions of intersections and 44,863 exits from the geometric model were reported.

TABLE 1

| | |
|---|---|
| 3,600,422 | univels having particle tracks |
| 33,670.034 | positions of intersection/sec |
| 1,212,263.3 | univels/sec |
| 36.004 | univels tracked through/position of intersection reported |
| 2.970 | elapsed time (sec) |
| 196,270.562 | distance traveled all particle tracks (cm) |
| 66,084.364 | distance traveled/sec |

It should be appreciated that since the simulated particle transport was performed in less than about 0.2 hours, the foregoing represents an advance over the present state of the art by as much as 51 times. Heretofore, such simulated particle transport would routinely require as much as 10 hours of computational time or more.

EXAMPLE 2

The following represents the actual algorithm information used to simulate such advanced particle transport along a particle track as presented at the 1998 Radiation Protection and Shielding Division Topical Conference in Nashville, Tenn. in April. Note that the subject matter of this presentation was directed only to external neutron sources.

Data Initialization: The uniformly spaced medical image data is read into an array. The x-pixel-size, y-pixel-size, and z-pixel size along with the minimum value of each coordinate is stored so conversions between world coordinates (WC) and normalized array coordinates (NAC) can be easily made. Here, the NAC simply corresponds to a location in the array of univels. For example, any location in the array can be found by an ordered triple of nonnegative integers, i.e., lookup (x,y,z)=array (z (width×length)+y (width)+x). A univel in WC is A mm×B mm×C mm. Whereas the univel in NAC is 1×1×1, for example.

| | |
|---|---|
| Parameters: | A call to the movement of the particle along a particle track is of the form: |
| Track_Ray | (position_vector, direction_unit_vector, ptr_to_miss_flag, ptr_to_current_region, ptr_to_next_region, ptr_to_distance_to_next_region); |
| Input to algorithm: | |
| position_vector: | Initial position of particle track in WC |
| direction_unit_vector: | Normalized direction of particle track in WC |
| Output of algorithm: | |
| miss_flag: | Either hit a new region or exit the geometric model |
| current_region: | The region (univel) the particle track starts in |
| next_region: | The first region intersected |
| distance_to_next_region: | The distance to the next region (univel) in WC |

Algorithm Initialization Calculations: The initial position and direction must be converted from WC to NAC. The initial anatomical material is stored in current_region. If the particle track does not start inside the univel geometric model, an intersection point with the univel geometric model must be calculated and an artificial starting point is set at this boundary intersection with the outer univel.

Stepping Algorithm: Though the internal routines of the algorithms vary, each is based on using integer arithmetic to find univels that the ideal particle track passes through. Each investigated univel has a corresponding call to a function that looks up the anatomical material type of the univel at the given position. The stepping algorithm terminates when a univel of a new anatomical material type is found or the particle along the particle track exits the geometric model.

Algorithm Completion Calculations: The position of intersection is computed accurately or miss_flag is set to indicate the particle exited the geometric model without an intersection. The distance to this point is calculated in WC and returned in distance_to_next_region. The new material encountered is stored in next_region

EXAMPLE 3

The following data was presented at the 1998 conference in Nashville, Tenn. and is exemplary of a particle track having Y as a primary direction of movement, X is the secondary direction of movement increasing in 0.125 units of a Cartesian coordinate system and Z is the tertiary direction of movement increasing in 0.75 units. The initial starting position of the particle track after centering is $x_0=5.00$, $y_0=1.5$ and $z_0=10.125$. Truncating (trunc) is the rounding down function. Stepping along the primary direction of movement yields the following data with an error term being an integer in the range of −32,768 to 32,767:

TABLE 2

| x | y | z | trunc(x) | trunc(y) | trunc(z) |
|---|---|---|---|---|---|
| 5.000 | 1.5 | 10.125 | 5 | 1 | 10 |
| 5.125 | 2.5 | 10.875 | 5 | 2 | 10 |
| 5.250 | 3.5 | 11.625 | 5 | 3 | 11 |
| 5.375 | 4.5 | 12.375 | 5 | 4 | 12 |
| 5.500 | 5.5 | 13.125 | 5 | 5 | 13 |
| 5.625 | 6.5 | 13.875 | 5 | 6 | 13 |
| 5.750 | 7.5 | 14.625 | 5 | 7 | 14 |
| 5.875 | 8.5 | 15.375 | 5 | 8 | 15 |
| 6.000 | 9.5 | 16.125 | 6 | 9 | 16 |

The bulk of the corresponding stepping algorithm for this example is as follows:

```
ADDX=0.125*32768=4096
ADDZ=0.750*32768=24576
ADDX_DECERR=ADDX−32768
ADDZ_DECERR=ADDZ−32768
ERRX=(x_0−trunc(x_0))*32768+ADDX_DECERR=−28672
ERRZ=(z_0−trunc(z_0))*32768+ADDZ_DECERR=−4096
XI=trunc(x)
YI=trunc(y)
ZI=trunc(z)
BEGIN_LOOP
LOOKUP(XI,YI,ZI)
YI=YI+1
If(ERRX>=0)
   XI=XI+1
   ERRX=ERRX+ADDX_DECERR
Else
   ERRX=ERRX+ADDX
If(ERRZ>=0)
   ZI=ZI+1
   ERRZ=ERRZ+ADDZ_DECERR
Else
   ERRZ=ERRZ+ADDZ
END_LOOP
```

The next table shows the values computed by the algorithm. Notice that the error term, i.e., ERRX or ERRZ, is a pre-computation used to determine how XI and ZI will change in the next iteration, increasing by 1 if the error is greater than or equal to 0 and remaining the same otherwise. The steps are similar when the directions are allowed to be decreasing.

TABLE 3

| XI | YI | ZI | ERRX | ERRZ |
|---|---|---|---|---|
| 5 | 1 | 10 | −28672 | −4096 |
| 5 | 2 | 10 | −24576 | 20480 |
| 5 | 3 | 11 | −20480 | 12288 |
| 5 | 4 | 12 | −16384 | 4096 |
| 5 | 5 | 13 | −12288 | −4096 |
| 5 | 6 | 13 | −8192 | 20480 |
| 5 | 7 | 14 | −4096 | 12288 |
| 5 | 8 | 15 | 0 | 4096 |
| 6 | 9 | 16 | −28672 | −4096 |

This example was for each x, y and z increasing and y varying the most. The method would be similar for either x or z varying the most. Negative directions only cause minor complications wherein absolute values of the directions are used to compute the ADDx's. ERRx's are computed based on the distance to the ceiling side rather than the floor side of the initial univel from the initial point.

In the general case, there is some roundoff error since the initial positions and increments may not be expressed exactly as fractions of 32768. Using 32 bit arithmetic instead, an individual error is less than $2^{-31}$ ($\approx 4.66*10^{-10}$) and the error accumulates by at most that much on each iteration. In a 256×256×40 array of univels, the cumulative error could at worst be $256*2^{-31}=2^{-23}$ ($\approx 1.19*10^{-7}$) which is insignificant in most cases for two reasons. The algorithm yields only an approximate x, y, and z as an array position which is then refined to give a precise intersection that is not subject to this cumulative error. Also, the approximated particle movement follows very closely the same univels as the ideal particle track. Being off by at most $2^{-23}$ of a side length suggests that the approximate particle track reports a position of intersection not intersected by the ideal particle track less than 1 in 1,000,000 times. If the algorithm reports a position of intersection that is not verifiable, the particle movement along the particle track is simply allowed to continue. Any position of intersection distance returned is precise and verified.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

We claim:

1. A method for tracking a particle through a geometric model, the method comprising:
   arranging a plurality of substantially uniform volume elements into the geometric model;
   describing a movement of the particle through the geometric model with a particle track;
   traversing the particle along the particle track from one uniform volume element to another uniform volume element in integer based increments;
   determining a material of both the one uniform volume element and the another uniform volume element; and
   terminating the traversing the particle when the material of the another uniform volume element is substantially different from the material of the one uniform volume element.

2. A method according to claim 1, further comprising converting a plurality of pixels of information contained in a medical image into the uniform volume elements.

3. A method according to claim 1, further comprising defining a material to be associated with each of the uniform volume elements.

4. A method according to claim 3, further comprising mapping each material associated with each of the uniform volume elements to an array.

5. A method according to claim 1, further comprising determining a position of intersection along the particle track where the material of the one uniform volume element changed into the material of the another uniform volume element.

6. A method according to claim 5, further comprising reporting the position of intersection.

7. A method according to claim 1, wherein the particle track has a primary direction of movement, further comprising traversing the particle along the particle track along the primary direction of movement.

8. A method according to claim 1, further comprising setting an initial condition for the particle track.

9. A method according to claim 8, wherein the particle traverses along the particle track beginning in a starting element of the uniform volume elements and traverses to a next element of the uniform volume elements, further comprising determining a center value of the starting element along a primary direction of movement for the particle track, the center value representing at least a portion of an adjusted coordinate from which the particle will begin traversal along the particle track.

10. A method according to claim 9, wherein the particle track has at least one secondary direction of movement, further comprising determining a beginning coordinate value for each secondary direction of movement in response to the determining the center value of the starting element along the primary direction of movement.

11. A method for tracking particle through a geometric model, the method comprising:
arranging a plurality of substantially uniform volume elements into the geometric model;
describing a movement of the particle through the geometric model with a particle track; and
traversing the particle along the particle track from one uniform volume element to another uniform volume element in integer based increments;
wherein the particle track has at least one secondary direction of movement, and further comprising calculating an error term for each secondary direction of movement, the error term being used to adjust a coordinate value whenever the error term exceeds a threshold value.

12. A method for simulating particle transport through a geometric model, the method comprising:
arranging a plurality of substantially uniform volume elements into the geometric model;
defining a material to be associated with each of the uniform volume elements, at least one of the uniform volume elements corresponding to a radiation source;
describing a particle track with a primary direction of movement through the geometric model, the particle track beginning substantially internally within the geometric model at the one of the uniform volume elements corresponding to the radiation source in a starting element of the uniform volume elements and traversing to a next element of the uniform volume elements; and following a particle along the particle track through the geometric model until the material of the next element is substantially different from the material of the starting element.

13. A method according to claim 12, wherein the describing the particle track comprises defining an initial position and a vector for the particle.

14. A method according to claim 12, wherein the defining the material to be associated with each uniform volume element further comprises mapping each material to an array.

15. A method according to claim 12, wherein the following the particle along the particle track comprises stepping along the particle track in integer based increments of the coordinate system along the primary direction of movement.

16. A method of computationally enlarging a radiation distribution for a treatment volume irradiated during radiation therapy having a radiation source substantially internal within a patient, the method comprising:
obtaining a medical image of the treatment volume, the medical image containing a plurality of pixels of information;
converting the pixels into a plurality of substantially uniform volume elements;
arranging the uniform volume elements into a geometric model;
defining a material to be associated with each uniform volume element, at least one of the uniform volume elements corresponding to the radiation source;
describing a plurality of particle tracks through the geometric model, the particle tracks beginning substantially internally within the geometric model at the one of the uniform volume elements corresponding to the radiation source having a primary direction of movement beginning in a starting element of the uniform volume elements and traversing to a next element of the uniform volume elements;
simulating a particle movement along each particle track of the plurality of particle tracks through the geometric model in integer based increments along the primary direction of movement until a position when the material of the next element is substantially different from the material of the starting element, the particle corresponding to an alpha, beta or gamma emission emanating from the radiation source during the radiation therapy, the position corresponding to at least one of the particles being captured, scattered and exited from the geometric model; and
computing a distribution of radiation doses based upon the particle movement along each of the particle tracks.

17. A method according to claim 16, further comprising generating a plurality of axial slices of the treatment volume.

18. A method according to claim 16, wherein the converting the pixels into the uniform volume elements further comprises proportionally convening a volume and shape of the pixels into a corresponding volume and shape of the uniform volume elements.

19. A computer readable medium having computer executable instructions, which when executed on a computer perform a process for tracking a movement of a particle through a geometric model, the computer executable instruction comprising instructions for:
arranging a plurality of substantially uniform volume elements into the geometric model;
mapping a material associated with each the uniform volume element to an array, at least one of the uniform volume elements being mapped to a radiation source;

projecting the movement of the particle through the geometric model with a particle track beginning in a starting element of the uniform volume elements and traversing to a next element of the uniform volume elements; and traversing the particle along the particle track in integer based increments until the material of the next element is substantially different from the material of the starting element.

20. A computer readable medium according to claim 19, further comprising computer executable instructions for storing the array in a storage device.

21. A computer readable medium according to claim 19, further comprising computer executable instructions for establishing a center value for the particle track along a primary direction of movement thereof.

22. A computer readable medium according to claim 19, further comprising computer executable instructions for storing the array by integers determined from a selected coordinate system.

23. A computer readable medium according to claim 22, further comprising computer executable instructions for computing error terms to be associated with at least one secondary direction of movement, the error terms being used to properly identify the materials stored in the array.

24. A computer readable medium according to claim 19, further comprising computer executable instructions for:

reading a medical image of a treatment volume irradiated by the radiation source having a plurality of pixels of information contained therein; and converting the pixels into the uniform volume elements.

25. A computer readable medium according to claim 24, further comprising computer executable instructions for proportionally converting a volume and shape of the pixels into a corresponding volume and shape of the uniform volume elements.

26. A computer readable medium according to claim 24, wherein the medical image comprises a plurality of substantially cross-sectional slices of the treatment volume, further comprising computer executable instructions for stacking the uniform volume elements into a three dimensional representation of the treatment volume.

27. A computer readable medium according to claim 19, further comprising computer executable instructions for displaying the geometric model.

28. A computer readable medium having computer executable instructions, which when executed on a computer perform a process for computationally enlarging a radiation distribution of a treatment volume irradiated during a radiation therapy having a radiation source, the computer executable instructions comprising instructions for:

reading a medical image of the treatment volume, the medical image containing a plurality of pixels of information;

converting the pixels into a plurality of substantially uniform volume elements;

mathematically arranging the uniform volume elements into a geometric model substantially representing the treatment volume;

mapping a material associated with each of the uniform volume elements to an array, at least one of the uniform volume elements corresponding to the radiation source;

describing a plurality of particle tracks through the geometric model, the particle tracks beginning substantially internally within the geometric model in a starting element of the uniform volume elements and traversing to a next element of the uniform volume elements;

simulating a particle movement along each particle track of the plurality of particle tracks through the geometric model in integer based increments until a position when the material of the next element is substantially different from the material of the starting element, the particle corresponding to an alpha, beta or gamma emission emanating from the radiation source during the radiation therapy, the position corresponding to at least one of the particle being captured, scattered and exited from the geometric model; and computing a distribution of radiation doses based upon the particle movement along each of the particle tracks.

29. A computer readable medium having computer executable modules including computer executable instruction, which when executed on a computer perform a process for enlarging a radiation distribution of a treatment volume irradiated during a radiation therapy having a radiation source, the modules comprising:

a reader module for converting a plurality of pixels of information contained in a medical image into a corresponding plurality of uniform volume elements;

a modeling module for arranging the uniform volume elements into a geometric representation of the treatment volume;

a storage module for storing a material for each of the uniform volume elements, at least one of the uniform volume elements being stored as corresponding to the radiation source;

a projection module for tracking a movement of a particle through the geometric representation according to integer based steps until a position when the material of a uniform volume element of the plurality is substantially different from the material of a starting element of the plurality of uniform volume elements; and a random generation module for calculating a status of the particle as the movement of the particle is tracked through the geometric representation.

30. A method for enlarging a radiation distribution of a treatment volume irradiated during a radiation therapy having a radiation source, the method comprising:

creating a geometric model of the treatment volume;

describing a movement having a primary direction and at least one secondary direction of a particle through the geometric model in integer based increments along the primary direction, the particle representing an alpha, beta or gamma emission emanating from the radiation source during the radiation therapy;

calculating an error term for each secondary direction, the error term being used to adjust a coordinate value whenever the error term exceeds a threshold value; and computing a distribution of radiation doses based upon the movement of the particle.

31. A method according to claim 30, wherein the geometric model is comprised of a plurality of substantially uniform volume elements, further comprising defining a material to be associated with each uniform volume element, at least one of the uniform volume elements corresponding to the radiation source.

32. A method according to claim 31, wherein the movement begins substantially internally within the geometric model in a starting element of the uniform volume elements arid traverses to a next element of the uniform volume elements, further comprising describing the movement of the particle through the geometric model until the material of the next element is substantially different from the material of the starting element.

33. A method according to claim 32, further comprising determining a position where along the movement, the material of the next element is substantially different from the material of the starting element.

34. A computer readable medium having computer executable instructions, which when executed on a computer perform a process comprising the acts as recited in claim 30.

35. A method for simulating particle transport through a geometric model, the method comprising:

arranging a plurality of substantially uniform volume elements into the geometric model;

defining a material to be associated with each of the uniform volume elements, at least one of the uniform volume elements corresponding to a radiation source;

describing a particle track with a primary direction of movement through the geometric model, the particle track beginning within a surface uniform volume element first encountered by a particle from an externally-applied radiation source and proceeding therefrom as if the particle track were born within the first surface uniform volume element; and following a particle along the particle track through the geometric model until the material of the next element is substantially different from the material of the starting element.

36. A method according to claim 35, wherein the describing the particle track comprises defining an initial position and a vector for the particle.

37. A method according to claim 35, wherein the defining the material to be associated with each uniform volume element further comprises mapping each material to an array.

38. A method according to claim 35, wherein the following the particle along the particle track comprises stepping along the particle track in integer based increments of the coordinate system along the primary direction of movement.

39. A method of computationally enlarging a radiation distribution for a treatment volume irradiated during radiation therapy having a radiation source external to a patient, the method comprising:

obtaining a medical image of the treatment volume, the medical image containing a plurality of pixels of information;

converting the pixels into a plurality of substantially uniform volume elements;

arranging the uniform volume elements into a geometric model;

defining a material to be associated with each of the uniform volume elements, at least one of the uniform volume elements corresponding to the radiation source;

describing a plurality of particle tracks through the geometric model, the plurality of particle tracks beginning within a surface uniform volume element first encountered by particles from an externally-applied radiation source and proceeding therefrom as if the plurality of particle tracks were born within the first surface uniform volume element; and simulating a particle movement along each particle track of the plurality of particle tracks through the geometric model in integer based increments along the primary direction of movement until a position when the material of the next element is substantially different from the material of the starting element, the particle corresponding to an alpha, beta or gamma emission emanating from the radiation source during the radiation therapy, the position corresponding to at least one of the particle being captured, scattered and exited from the geometric model; and computing a distribution of radiation doses based upon the particle movement along each of the particle tracks.

40. A method according to claim 39, further comprising generating a plurality of axial slices of the treatment volume.

41. A method according to claim 39, wherein the converting the pixels into the uniform volume elements further comprises proportionally converting a volume and shape of the pixels into a corresponding volume and shape of the uniform volume elements.

42. A computer readable medium having computer executable instructions, which when executed on a computer perform a process for computationally enlarging a radiation distribution of a treatment volume irradiated during a radiation therapy having a radiation source, the computer executable instructions comprising instructions for:

reading a medical image of the treatment volume, the medical image containing a plurality of pixels of information;

converting the pixels into a plurality of substantially uniform volume elements;

mathematically arranging the uniform volume elements into a geometric model substantially representing the treatment volume;

mapping a material associated with each uniform volume element to an array, at least one of the uniform volume elements corresponding to the radiation source;

describing a plurality of particle tracks through the geometric model, the plurality of particle tracks beginning within a surface uniform volume element first encountered by particles from an externally-applied radiation source and proceeding therefrom as if the plurality of particle tracks were born within the first surface uniform volume element; and simulating a particle movement along each particle track of the plurality of particle tracks through the geometric model in integer based increments until a position when the material of the next element is substantially different from the material of the starting element, the particle corresponding to an alpha, beta or gamma emission emanating from the radiation source during the radiation therapy, the position corresponding to at least one of the particle being captured, scattered and exited from the geometric model; and computing a distribution of radiation doses based upon the particle movement along each of the particle tracks.

* * * * *